(12) United States Patent
Park et al.

(10) Patent No.: US 8,951,567 B2
(45) Date of Patent: Feb. 10, 2015

(54) SOL-GEL PHASE-REVERSIBLE HYDROGEL TEMPLATES AND USES THEREOF

(75) Inventors: Kinam Park, West Lafayette, IN (US); Ghanashyam Acharya, West Lafayette, IN (US); Haesun Park, West Lafayette, IN (US)

(73) Assignee: Akina, Inc., West Lafayette, IN (US)

( * ) Notice: Subject to any disclaimer, the term of this patent is extended or adjusted under 35 U.S.C. 154(b) by 1083 days.

(21) Appl. No.: 12/286,147

(22) Filed: Sep. 27, 2008

(65) Prior Publication Data

US 2009/0136583 A1   May 28, 2009

Related U.S. Application Data

(60) Provisional application No. 60/995,693, filed on Sep. 27, 2007, provisional application No. 61/066,376, filed on Feb. 19, 2008.

(51) Int. Cl.
*A61K 9/14* (2006.01)
*A61K 9/50* (2006.01)
*A61K 31/00* (2006.01)
(Continued)

(52) U.S. Cl.
CPC ............. *A61K 9/5031* (2013.01); *A61K 9/5089* (2013.01); *A61K 31/00* (2013.01); *Y10S 977/773* (2013.01); *Y10S 977/887* (2013.01); *Y10S 977/89* (2013.01); *Y10S 977/906* (2013.01)
USPC ........ 424/497; 506/30; 427/213.36; 977/773; 977/887; 977/890; 977/906

(58) Field of Classification Search
CPC ....... A61K 31/00; A61K 9/50; A61K 9/5031; A61K 9/5089
See application file for complete search history.

(56) References Cited

U.S. PATENT DOCUMENTS

| 4,381,963 A * | 5/1983 | Goldstein et al. ............. 156/245 |
| 6,277,768 B1 * | 8/2001 | Mumick et al. ................. 442/59 |

(Continued)

OTHER PUBLICATIONS

Desai, Manisha P., et al.; "The Mechanism of Uptake of Biodegradable Microparticles in Caco-2 Cells is Size Dependent", 1997, Plenum Publishing Group; Pharmaceutical Research, vol. 14, No. 11, pp. 1568-1573.*

(Continued)

*Primary Examiner* — Suzanne Ziska
*Assistant Examiner* — Ivan Greene
(74) *Attorney, Agent, or Firm* — Fish & Richardson P.C.

(57) ABSTRACT

Discrete microstructures of predefined size and shape are prepared using sol-gel phase-reversible hydrogel templates. An aqueous solution of hydrogel-forming material is covered onto a microfabricated silicon wafer master template having predefined microfeatures, such as pillars. A hydrogel template is formed, usually by lowering the temperature, and the formed hydrogel template is peeled away from the silicon master template. The wells of predefined size and shape on the hydrogel template are filled with a solution or a paste of a water-insoluble polymer, and the solvent is removed to form solid structures. The formed microstructures are released from the hydrogel template by simply melting the hydrogel template in water. The microstructures are collected by centrifugation. The microstructures fabricated by this method exhibit pre-defined size and shape that exactly correspond to the microwells of the hydrogel template. The method of preparing microstructures based on hydrogel templates is simple and can easily produce large quantities of the microstructures.

17 Claims, 5 Drawing Sheets

(51) Int. Cl.
B82B 1/00 (2006.01)
B82B 3/00 (2006.01)

(56) References Cited

U.S. PATENT DOCUMENTS

| | | | |
|---|---|---|---|
| 6,767,637 B2* | 7/2004 | Park et al. | 428/402.21 |
| 7,125,639 B2 | 10/2006 | Schaper | |
| 7,375,404 B2* | 5/2008 | Park et al. | 257/414 |
| 2003/0104347 A1 | 6/2003 | Mori et al. | |
| 2004/0115279 A1* | 6/2004 | Hansford et al. | 424/489 |
| 2004/0191321 A1* | 9/2004 | Guan et al. | 424/489 |
| 2004/0247912 A1* | 12/2004 | Kim | 428/500 |
| 2005/0208465 A1* | 9/2005 | Arai et al. | 435/4 |
| 2007/0031505 A1 | 2/2007 | Roy et al. | |
| 2007/0065481 A1 | 3/2007 | Chudzik et al. | |
| 2007/0110962 A1 | 5/2007 | Tien et al. | |
| 2007/0116771 A1 | 5/2007 | Sung et al. | |
| 2007/0190154 A1* | 8/2007 | Zeigerson | 424/489 |
| 2007/0264481 A1 | 11/2007 | DeSimone et al. | |

OTHER PUBLICATIONS

Guan, Jingjiao; Chakrapani, Aravind; and Hansford, Derek J.; "Polymer Microparticles Fabricated by Soft Lithography", 2005, American Chemical Society, vol. 17, No. 25, pp. 6227-6229.*

Vozzi, Giovanni et al.; "Fabrication of PLGA scaffolds using soft lithography and microsyringe deposition", 2003, Elsevier, Biomaterials, vol. 24, pp. 2533-2540.*

Tao, Sarah L. and Desai, Tejal A.; "Microfabrication of Multilayer, Asymmetric, Polymeric Devices for Drug Delivery", 2005, WILEY-VCH, Advanced Materials, vol. 17, pp. 1625-1630.*

Guan, Jingjiao; Ferrell, Nicholas; Lee, James L.; Hansford, Derek J.; "Fabrication of polymeric microparticles for drug delivery by soft lithography", 2006, Elsevier, Biomaterials, vol. 27, pp. 4034-4041.*

Paguirigan, A. and Beebe, D. J.; "Gelatin based microfluidic devices for cell culture", 2006, Royal Society of Chemistry; Lab on a Chip, vol. 6, pp. 407-413.*

Acharya, Ghanashyam et al.; "The hydrogel template method for fabrication of homogeneous nano/microparticles", 2010, Elsevier, Journal of Controlled Release, vol. 141, pp. 314-319.*

Acharya, Ghanashyam et al.; "A study of drug release from homogeneous PLGA microstructures", 2010, Elsevier, Journal of Controlled Release, vol. 146, pp. 201-206.*

Yoshioka, Hiroshi et al.; "Thermoreversible Gelation on Cooling and on Heating of an Aqueous Gelatin-Poly(N-isopropylacrylamide) Conjugate", 1998, John Wiley & Sons.; Polymers for Advanced Technologies, vol. 2, Issue 2, pp. 155-158.*

Golden, Andrew P. and Tein, Joe; "Fabrication of microfluidic hydrogels using molded gelatin as a sacrificial element", 2007, The Royal Society of Chemistry, Lab on a Chip, vol. 7, Issue 6, pp. 720-725.*

Chakrapani, Aravind; "Processing and characterization of polymer microparticles for controlled drug delivery systems" Ph.D. dissertation (2006), The Ohio State University, United States—Ohio. Retrieved Mar. 9, 2011, from Dissertations & Theses: Full Text. (Publication No. AAT 3238236), pp. 1-107.*

Xia, Jingwei et al.; "Microparticles developed by electrohydrodynamic atomization for the local delivery of anticancer drug to treat C6 glioma in vitro", 2006, Elsevier, Biomaterials, vol. 27, Issue 17, pp. 3321-3332.*

Tsung, M. Jamie and Burgess, Diane J.; "Preparation and Characterization of Gelatin Surface Modified PLGA Microspheres", 2001, Springer, The AAPS Journal, vol. 3, Issue 2, pp. 14-24 (pp. 1-11 as provided).*

Jeong. B. at al., Thermosensitive sol-gel reversible hydrogels, 2002. Advanced Drug Delivery Reviews, vol. 54, pp. 37-51.

Yoon, D. et al., Natural and synthetic polymeric scaffolds, 2009. Biomedical Materials. R. Narayan, ed., Springer. pp. 415-442.(see p. 420).

Koob. T., et al., Mechanical and thermal properties of novel polymerized NDGA-gelatin hydrogels, 2003. Blomaterials, vol. 24, pp. 1285-1292.

Landers, R. et al., Rapid prototyping of scaffolds derived from thermoreversible hydrogels and tailored for applications in tissue engineering, 2002, Biomaterlals, vol. 23, pp. 4437-4447.

Schift, H., Nanoimprint lithography: an old story in modern times? A review, 2008. J. Vac. Sci. Technol. B26, 458-479.

Truskett, V. et al., Trends in imprint lithography for biological applications, 2006. Trends Biotechnol. 24, 312-317.

Schaper, C., Molecular transfer lithography for pseudomaskless, high-throughput, aligned nanolithography, 2003. J. Vac. Sci. Technol. 2961-2965.

Xia, Y. et al., Soft lithography, 1998. Annu. Rev. Mater. Sci., 28, 153-184.

Yan, L., et al., Patterning thin films of poly(ethylene imine) on a reactive SAM using microcontact printing, 1999. Langmuir, 15, 1208-1214.

Zhao, X.-M., et al., Fabrication of three-dimensional micro-structures: Microtransfer molding, 1996. Adv. Mater. 8(10), 837-840.

Wang, M., et al., Patterning polymers by micro-fluid-contact printing, 2001. Adv. Mater. 13, 1312-1317.

Guan, J., et al., Polymer microparticles fabricated by soft lithography, 2005. Chem. Mater. 17, 6227-6229.

Rolland, J., et al., Direct fabrication and harvesting of monodisperse, shape-specific nanobiomaterials, 2005. J. Am. Chem. Soc. 127, 10096-10100.

Kelly, J., et al., Shape-specific, monodisperse nano-molding of protein particles, 2008. J. Am. Chem. Soc. 130, 5438-5439.

* cited by examiner

SOL-GEL PHASE-REVERSIBLE HYDROGEL TEMPLATES AND USES THEREOF

REFERENCE TO RELATED APPLICATIONS

The present application claims the benefit of U.S. Provisional No. 60/995,693, filed Sep. 27, 2007, and U.S. Provisional No. 61/066,376, filed Feb. 19, 2008, the disclosures of which are incorporated herein by reference.

FIELD OF THE INVENTION

The present invention relates to hydrogel templates and their use in fabricating nano/micro structures containing pharmacologically active ingredients and diagnostic agents.

BACKGROUND OF THE INVENTION

For long-term drug delivery, ranging from days to months, the parenteral administration of particles in the nano- or micro-scale has been widely used. The nano/micro particles are easy to administer using conventional needles. They have also been used for oral administration of various drugs. Despite extensive applications of the nano/micro particulate systems, the development of clinically useful products has been slow, and only a limited number of clinical products are available. As used herein, "nano" refers to nanoparticles and processes wherein the scale is in the range 1 nanometer (nm) to 1 micrometer (μm). As used herein, "micro" refers to particles and processes in the range of 1 μm to 1000 μm. When it is not necessary to distinguish between nano and micro sizes, the term "micro" is used generically to refer to objects in both the nano- and micro-size ranges.

The slow development of clinically successful formulations is due to several reasons. For example, the drug loading efficiency in microparticles is in general very low; typically below 10% for most drugs, especially protein drugs. Even for those drugs with higher loading efficiency, e.g., 10-20%, the majority of the drug is lost during preparation. This may be acceptable for low cost drugs, but most protein drugs are very expensive and such losses would not be acceptable for any formulations. One of the reasons for such losses is that the water-soluble drugs in the microparticles are exposed to a large amount of water before microparticles become solidified during preparation by emulsion methods, which are the most common method for microparticle preparation. Additionally, current emulsion methods are difficult to scale-up for mass production and result in heterogeneous particle size distributions. Recent advances in nanotechnology, especially in nano/micro fabrication (collectively microfabrication) and manufacturing processes have provided new avenues of making pharmaceutical formulations.

The development of high resolution microfabrication technologies has revolutionized the microelectronics and microdevice industry. By using microfabrication methods, such as photolithography and electron beam (E-beam) lithography, silicon and glass templates with micro and nano features have been developed. In the last few years, several microfabrication methods have been developed as alternatives to E-beam and photolithography that can achieve high resolution without compromising the feature integrity. In addition, these methods possess greater versatility in materials and processing approaches than silicon-based microfabrication techniques. These new printing methods include nanoimprint lithography [H. Schift], step and flash imprint lithography [V. Truskett, et al.], molecular transfer lithography [C. Schaper], and soft lithography [Y. Xia, et al.]. These methods use either microfabricated silicon or glass templates, or polymeric templates with special properties, to form patterns on various substrates.

Nano-imprint lithography (NIL) is a high-resolution patterning method in which a surface pattern of a stamp is replicated into a material by mechanical contact and three dimensional materials displacement. The major advantage of NIL is the ability to pattern sub-25 nm structures over a large area with a high-throughput and low-cost. Step and flash imprint lithography (S-FIL) is distinguished from NIL by being a UV-assisted nanoimprint technique that molds photocurable liquids rather than heat-assisted molding of polymer-coated wafers.

Molecular transfer lithography (M×L) is used for replication of surface patterns as water-soluble templates. The templates are prepared by spin-casting a poly(vinyl alcohol) (PVA) solution on a silicon master pattern. The resultant water-soluble templates are dried and then bonded to another substrate using an intervening adhesive layer that solidifies through photocuring, thermal curing, or two-part reactive schemes. The templates are chemically removed by dissolution with water yielding a formed pattern in the adhesion layer. See, e.g., U.S. Pat. No. 7,125,639 issued to Schaper.

Soft lithography is a collective name for a group of non-photolithographic microfabrication techniques using an elastomeric stamp with relief features to generate microstructures. Among the soft lithographic techniques, microcontact printing [Yan et al.], microtransfer molding [Zhao et al.], and microfluid contact printing [Wang et al.] have produced isolated polymer structures. Soft lithography methods use hydrophobic polymer (e.g., poly(dimethyl siloxane), or PDMS) templates for imprinting. These methods enable preparation of soft material templates using organic polymers, biopolymers, and inorganic materials.

Currently available nano- and micro-particulate drug delivery systems are made mainly by emulsion methods. The emulsion methods result in a highly polydispersed population of particles, and their physico-chemical characteristics, degradation kinetics, material properties and drug release profiles represent only the average values of the particles. Since the particles are highly heterogeneous, it is difficult to examine the effect of size on biological responses due to wide distribution of the particle size. Furthermore, the presence of particles much larger than the average size makes it difficult to develop clinically useful delivery systems. Microfabrication techniques allow preparation of monodisperse particles. Several soft lithography-based strategies have been developed in combination with a lift-off approach to prepare homogeneous particles. These strategies enable fabrication of microstructures made of drug-containing polymers, even though the processes require substantial improvement for easy collection in large quantities.

MicroContact Hot Printing (μCHP) has been developed to prepare thin-film microparticles with well-defined shapes using thermoplastic polymers [Guan, et al.]. This method selectively transfers polymer features from a continuous film on a stamp to a substrate. By this method, microparticles of thermoplastic polymers, such as poly(lactic-co-glycolic acid) (PLGA), polycaprolactone (PCL), poly(methyl methacrylate) (PMMA), and polystyrene have been prepared [See, e.g., U.S. Pat. Pub. 2004/0115279]. This method suffers from several limitations, however. First, control of the thickness of the microparticles is very difficult as it depends on the complete transfer of the polymer solution from the PDMS stamp to the release slide. This results in formation of microparticles with non-uniform thicknesses. Although the lateral size of the microparticles can be controlled, the vertical size (i.e., the thickness) of the microparticles cannot be exactly controlled. Second, this method is useful only with dilute polymer solutions (1-7%), as it involves filling of the microwells of the template by dipping into a polymer solution. At higher concentrations, the polymer solutions are highly viscous and difficult to fill the wells, as the polymer solutions tend to form a continuous polymer film on the surface of the template. Third, since most of the polymers are soluble only in organic solvents, the solvent can diffuse into the PDMS matrix thus damaging the stamp and preventing smooth release of the microparticles from the wells.

Step and Flash Imprint Lithography (S-FIL) has been used for fabrication of nanoparticles of precise sizes. S-FIL is a commercially available nano-molding process that utilizes the topography of a quartz template to mold UV crosslinkable macromers into patterns on a silicon wafer. [See, U.S. Pat. Pub. 2007/0031505]. Although this method produces nanoparticles, it has serious limitations. First, it involves the in situ photopolymerization of the macromers in the quartz template. This may cause concerns about the purity of the produce particles for clinical applications. Second, some photoinitiator molecules will remain active in the nanoparticles that can react with other biomolecules present in the human body, potentially leading to serious side effects. Third, exposure of the imprinted particles to oxygen plasma during isolation results in the formation of reactive ions on the nanoparticle surface and can also degrade the drug molecules.

Particle replication in nonwetting templates (PRINT) has been developed for making microparticles using fluoropolymer-based templates. Monodisperse polymer particles ranging from sub-200 nm to micron-scale structures of poly(ethylene glycol diacrylate), triacrylate resin, poly(lactic acid) (PLA), and polypyrrole have been fabricated by this method. PRINT uses chemically resistant fluoropolymers as molding materials, which eliminates the formation of a residual interconnecting film between molded objects. [See, e.g., U.S. Pat. Pub. 2007/0264481]. The PRINT mold has been used in fabrication of polymer and protein microparticles [Rolland, et al., Kelly et al.]. The PRINT method has demonstrated the use of non-wetting templates based on fluoro polymers for fabrication of microparticles for various applications. However, practical applications of the PRINT method are limited by the multi-step PFPE template preparation and laborious particle harvesting procedures. For example, the PRINT particles are harvested from the wafer either using physical scraping with surgical blades or by shear force using a glass slide, both of which are not practical and could damage the particles, and thus they may not be suitable for large scale manufacturing. Also, the PRINT particles harvested by using in situ polymerizable cyanoacrylate harvesting films may lead to adsorption of reactive monomers onto the PRINT particles leading to surface contamination.

The methods described above, namely μCHP, S-FIL, and PRINT, are able to produce micro- and nano-particles of homogeneous size and shape, but they have several limitations for practical applications of developing clinically useful drug delivery particles. First, the methods generally require in situ polymerization of the macromers in the template wells as seen in S-FIL and PRINT. This leads to a concern about the purity of the microparticles for human applications. Second, the methods are unable to control the thickness of the microparticles as seen in μCHP. Third, the methods are compatible with only certain materials. Fourth, the methods require multi-step and laborious microparticle harvesting procedures. The rigorous conditions, including highly aggressive solutions and elevated temperatures, which are used to release fabricated microparticles into solution may damage fragile compounds that have been incorporated into the microparticles. Thus, there are significant limitations to using currently available fabrication methods for the preparation of microstructures. In summary, there exists a critical need for development of new template preparation methods and new materials for use in the fabrication of homogeneous microstructures with various sizes and shapes for applications in drug delivery.

SUMMARY OF THE INVENTION

Microparticles are prepared according to principles of the present invention by employing a sol-gel phase-reversible hydrogel template, which is provided with a plurality of wells/cavities. A hydrogel template of the invention is ultimately formed from a master template, which is preferably made from a silicon wafer using conventional photolithographic techniques. Such etching techniques can be employed to design in the master template pillars having a wide variety of shapes, e.g., circular, rectangular, diamond-shaped, etc., so that the hydrogel template possesses wells of the same shapes of the pillars in the silicon master template.

A hydrogel template of the present invention can either be formed (i) directly from the silicon master template, or (ii) indirectly via an intermediate polymer template. Thus, regarding the hydrogel template as having a positive image of the desired plurality of wells, option (i) entails forming a negative image master template. For option (ii), the master template would have a positive image substantially identical with the hydrogel template. The intermediate polymer template having the negative image is conveniently formed from a conventional mold polymer, such as poly(dimethyl siloxane), or PDMS.

Employing either the master template or optional polymer template, a layer of a sol is coated thereon. The sol is then converted to a gel to form the hydrogel template, which is separated from the master or polymer template. The present invention affords sol-gel phase-reversible hydrogel templates wherein the designed cavities have a size in the range of about 100 nm to about 1,000 μm, preferably in the range of 200 nm to 200 μm, more preferably in the range of 500 nm to 100 μm.

In another aspect of the invention, nanoparticles or microparticles are prepared by a method that comprises filling a plurality of wells in a hydrogel template with a nonaqueous solution having a water-insoluble polymer dissolved therein, which preferably also contains a bioactive agent. The water-insoluble polymer is solidified in the wells by evaporating solvent from the nonaqueous solution. The nanoparticles or microparticles can then be harvested from the hydrogel template, e.g., by dissolving the hydrogel in aqueous solution. In another embodiment, the hydrogel template containing microparticles can be cut into suitable sizes and freeze dried (lyophilized), e.g., in a vial. The latter embodiment permits ready reconstitution simply by adding aqueous solution.

Previous microfabrication processes have not utilized hydrogel templates to make microparticles in the desired size range. The present invention makes it much easier to form and collect nano- and micro-sized particles, and the simple processing steps allow easy scale-up. Furthermore, the present invention affords extremely high drug loading efficiencies up to 50%, which are not possible with conventional methods. Preferred bioactive agents loaded into the particles include low molecular weight drugs, such as paclitaxel, sirolimus, probucol, and griseofulvin, as well as high molecular weight drugs, e.g., in powdered form, such as protein drugs including immunoglobulins, growth factors, insulin, interferons and erythropoietin.

DESCRIPTION OF THE DRAWINGS

FIG. 1 shows a schematic depiction of a microparticle fabrication procedure according to principles of the present invention. The sequence shows fabrication of a silicon wafer master template (A), formation of a hydrogel template (B and C), formation of microstructures by filling the cavities in the hydrogel template (D), dissolution of the hydrogel template in aqueous solution (E), and collection of collection of individual microstructures (F).

DETAILED DESCRIPTION OF THE INVENTION

The present invention will now be described in detail with reference to the Figures and Examples presented herein below.

Preparation of Silicon Wafer Master Templates

A silicon wafer master template is fabricated following a well-established technique. Photoresist (positive, AZ-1518) is coated onto a clean, oxidized (5000 Å) Si wafer with a spin-coater. After the positive photoresist process, the Si wafer is inserted into buffered hydrofluoric acid solution to etch silicon dioxide. After the photoresist is removed, the wafer is immersed in tetramethyl ammonium hydroxide to etch silicon. The etched Si wafer master template is used for further processing. The dimension of the holes etched on the Si wafer is varied to obtain holes with different diameters and depths. Not only the dimension but also the shape of the holes can be varied. A variety of shapes, such as circle, triangle, rectangle, and star, will be very useful in applications where distinction based on the shape is important.

UV Photolithography for Patterns of 10 µm and 50 µm

Photolithography masks of different sizes and shapes (e.g., circle, rod, diamond, and triangle) can be designed by using Auto CAD 2007 program, and the masks fabricated by TR Electromask XX251 instrument. A 4" silicon wafer covered with 1 µm thick $SiO_2$ layer (University Wafer) is spin coated with hexamethyl disilazine (Mallinckrodt) at 3,500 rpm for 30 sec (SCS P6708 Spin Coater from Specialty Coating Systems). The silicon wafer is then spin coated with a pohotoresist AZ9260 (Microchemicals GmbH) at 1000 rpm for 30 sec to form a uniform 10 µm thick photoresist film. Then, the wafer is soft baked at 90° C. for 10 min to remove solvent and moisture. The photoresist coated silicon wafer is exposed to UV light (23 mW/cm$^2$) for 26 sec using a mask aligner (Karl Suss MJB-3), followed by development with AZ 400K developer (Microchemicals GmbH) for 2 min with continuous agitation. The developed silicon wafer is rinsed with water and dried under a stream of nitrogen gas.

E-Beam Lithography for Patterns of 50 nm 100 nm, 300 nm, 500 nm, and 1 µm

UV-photolithography has a limit of resolution of 1 µm size and is not useful for nanofabrication of features below 1 µm. On the other hand, E-beam lithography has a resolution range between 1 µm to 10 nm. E-beam lithography uses high power electron beam to produce very highly focused electron beam that can write very fine features with very high resolution. For fabrication of silicon master templates using E-beam lithography, the following process is used. A 3" silicon wafer covered with 1 µm thick $SiO_2$ layer (University Wafer) is spin coated with poly(methyl methacrylate) (PMMA, Microchem) photoresist of 300 nm thick layer using a spin coater at 3,500 rpm for 30 sec. The coated PMMA photoresist layer is exposed to an electron beam in a preprogrammed pattern using Leica VB-6 Ultra-High Resolution, Extra-Wide Field Electron Beam Lithography Tool (operating at 100 KV, transmission rate 25 MHz, current 5 nA). After E-beam lithography, the silicon wafer is developed in 3:1 isopropanol: methyl isobutyl ketone solution. Onto this pattern a 5 nm Cr and 20 nm Au is deposited using Varian E-Beam Evaporator, followed by liftoff of the residual PMMA film in refluxing acetone. The pattern is transferred to the underlying silicon oxide by reactive ion etching (STS Reactive Ion Etch (RIE) Systems). The silicon master template is examined under a field-emission scanning electron microscope (FESEM, Hitachi S-4800) to characterize the size, shape, and integrity of the patterns.

Production of Microparticles of Predefined Geometries from Hydrogel Templates

A key aspect of this invention is to utilize sol-gel phase-reversible hydrogel templates for making microstructures. The general procedure of making a hydrogel template for easy harvesting of prepared microstructures is illustrated schematically in FIG. 1. Steps A-F show microfabrication of microparticles from a master template utilizing a hydrogel template: (A) A pattern is formed on a silicon wafer master template; (B) a gelatin solution is placed on top of the master template and lower the temperature to form a hydrogel imprint (sol-to-gel phase transition); (C) after the gelatin layer is solidified, the gelatin mold is peeled off exposing cavities; (D) the cavities in a hydrogel mold are filled by smearing a drug/PLGA solution or a paste with a blade; (E) the gelatin mold is dissolved by increasing the temperature in a water bath (gel-to-sol phase transition); and (F) individual particles are collected by centrifugation.

Figure 1:
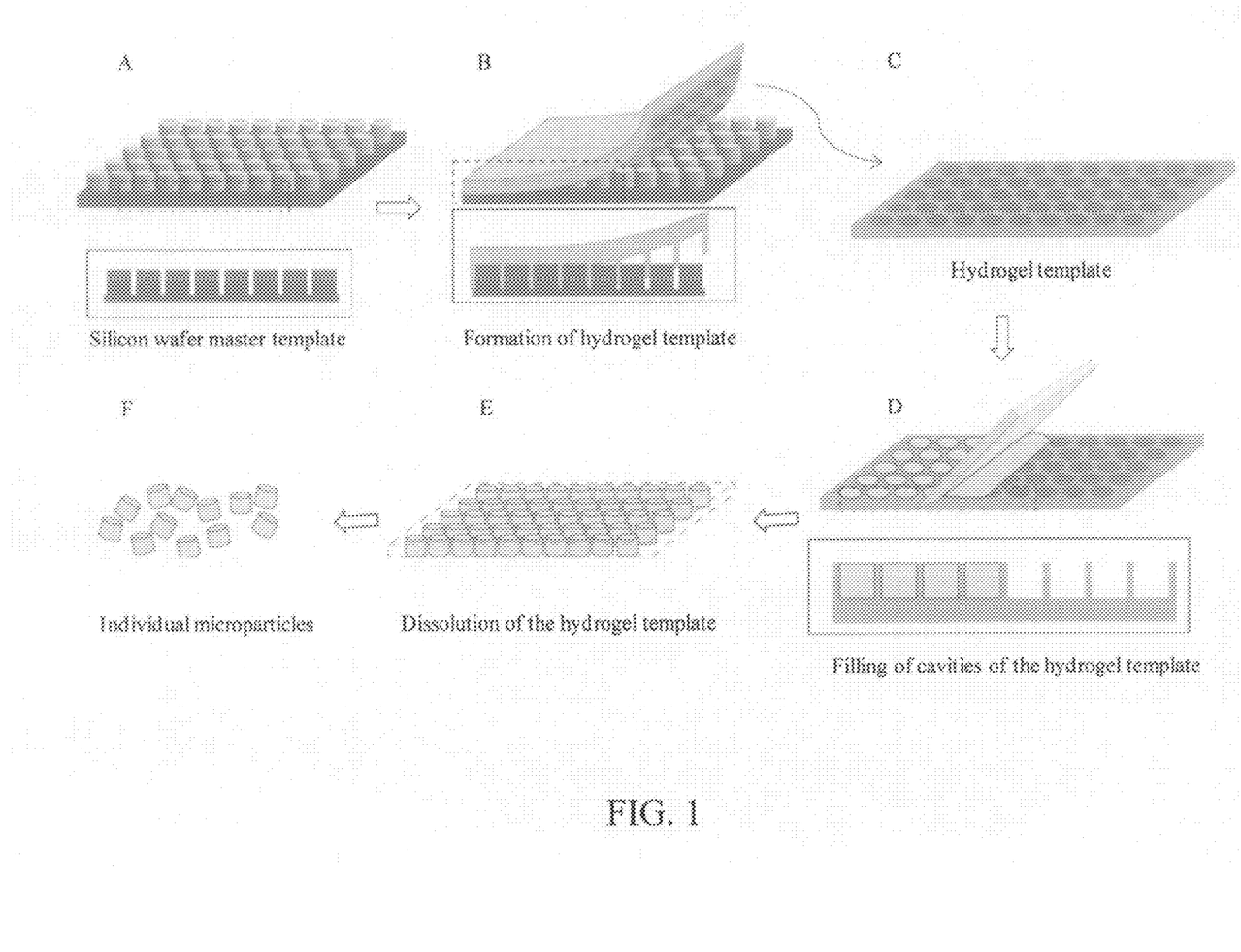
Figure 2:
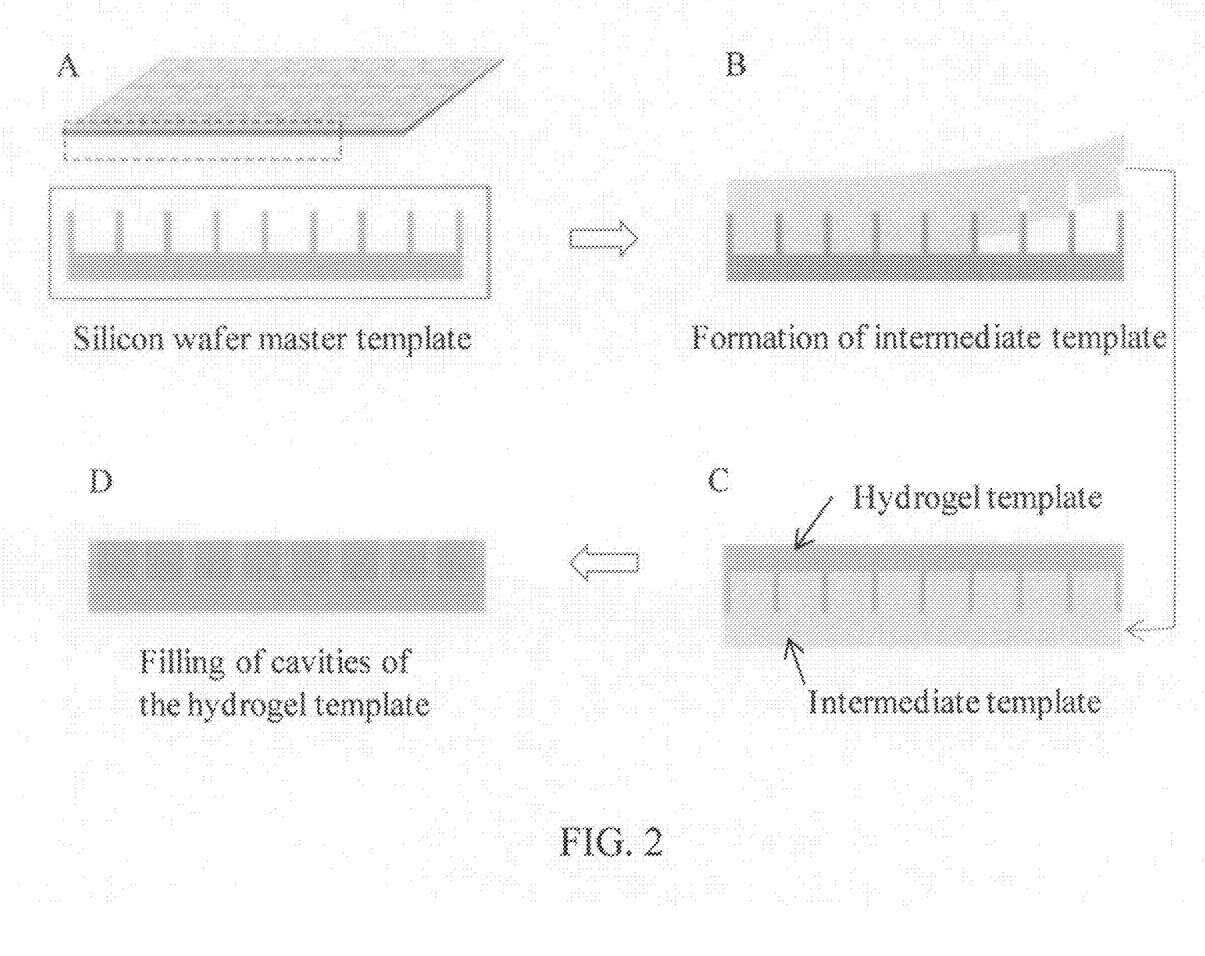
FIG. 2 shows a schematic depiction of a microparticle fabrication procedure using an intermediate polymer template and a hydrogel template. The sequence shows fabrication of a silicon wafer master template (A), formation of an intermediate polymer template, e.g., PDMS template (B), formation of a hydrogel template using the intermediate polymer template (C), and formation of microstructures by filling the cavities in the hydrogel template (D). The formed microstructures can be collected as described in Steps E and F of FIG. 1.

In a variation of the method described in FIG. 1, an intermediate polymer template, such as PDMS intermediate template, can be fabricated before making hydrogel templates. As shown in FIG. 2, an intermediate polymer template can be fabricated using a polymer, such as poly(dimethyl siloxane) (PDMS) (Sylgard® 184 silicone elastomer). The blend of elastomeric monomer and curing agent in a 10:1 (w/w) ratio is mixed thoroughly. The mixture is poured on top of the silicon wafer master template in a container, e.g., glass Petri dish. The container is then placed in vacuum for 10 min to remove air bubbles, and then transferred to a 70° C. chamber for curing for 30 min. The PDMS intermediate template is peeled off from the Si master template (FIG. 2B), and the PDMS intermediate template is used for preparing a hydrogel template (FIG. 2C).

A hydrogel template is formed by applying a solution of a hydrogel-forming material on either the master template surface or the intermediate polymer template surface. A hydrogel template is formed via a sol-gel phase transition taking place on the surface. The sol-gel conversion is induced, e.g., by changing temperature, introducing multivalent ions, or drying. Once formed, the hydrogel template is simply peeled away from the master template or intermediate template. Exemplary hydrogel templates formed in this fashion can comprise natural polymers such as gelatin, agarose, chitosan and alginate.

As shown in FIG. 1, one method of manufacturing microparticles according to the present invention comprises applying a mixture of a bioactive agent and polymer dissolved in a nonaqueous solvent to the plurality of wells of the hydrogel template so that the wells are filled with the drug/polymer mixture. The drug/polymer mixture can be applied as a solution or paste, which can be subsequently hardened, e.g., by solvent evaporation. The paste form allows incorporation of high concentrations of a bioactive agent and the polymer, and the paste can be pressure filled into the wells of the hydrogel template. The filled hydrogel templates are then placed in aqueous solution to induce a phase change from gel to sol to release individual drug/polymer microstructures, which can be subsequently collected by filtering and/or centrifugation. The microstructures fabricated accordingly exhibit well-defined geometries that exactly correspond to the microwells of the hydrogel template. Typically, the microstructures have a diameter in the range of about 100 nm to about 1000 μm, preferably about 200 nm to about 200 μm, more preferably about 500 nm to about 100 μm, and most preferably about 1 μm to about 50 μm.

Figure 3:
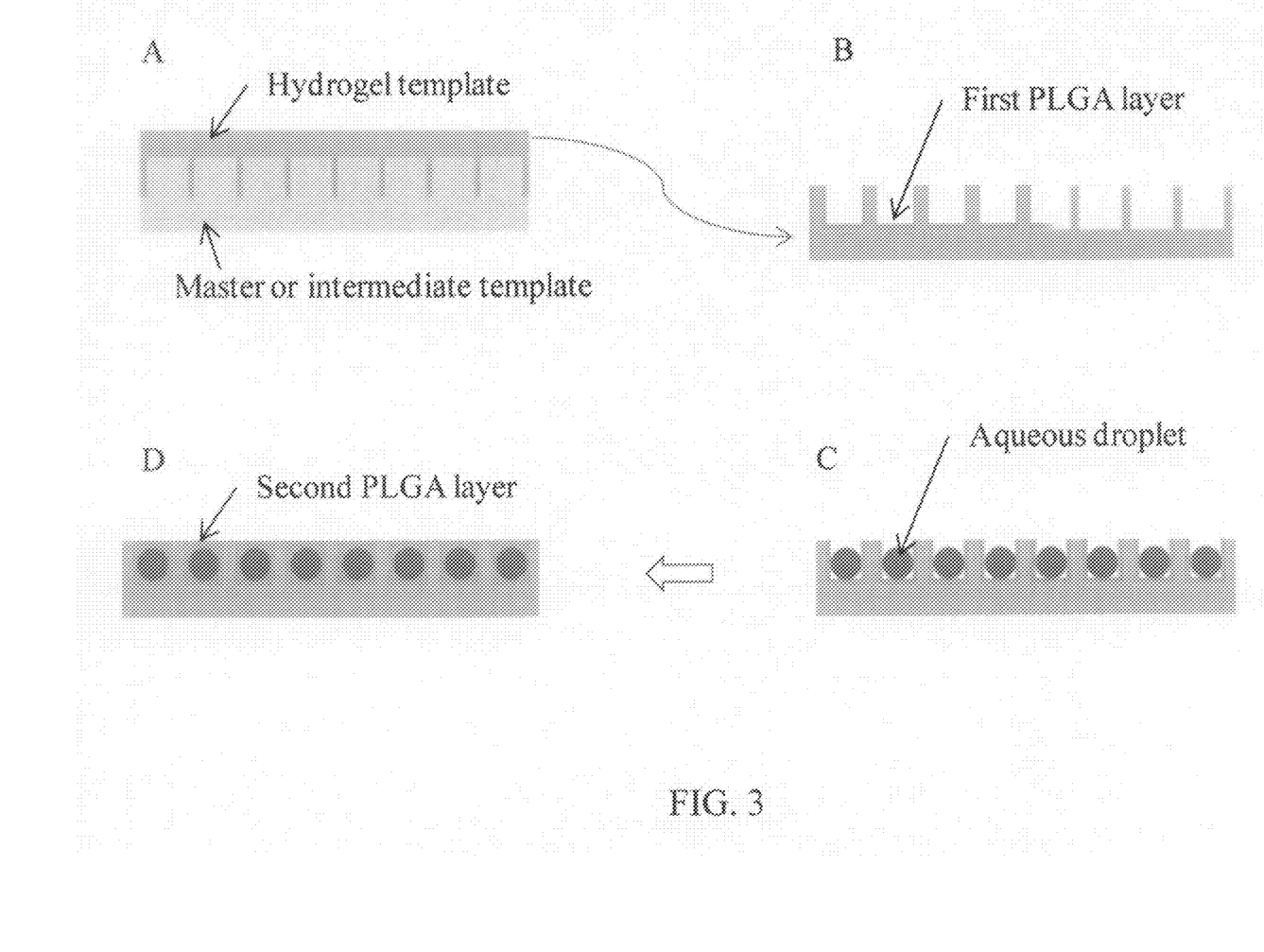
FIG. 3 shows a schematic depiction of the fabrication procedure for making microparticles in which the aqueous core is covered by a water-insoluble polymer, e.g., PLGA. The sequence shows formation of a hydrogel template using either the silicon wafer master template or intermediate polymer template (A), formation of the initial PLGA layer by spin coating or spray coating (B), filling the wells with aqueous droplets (C), and covering the cavities with the second layer of PLGA to seal the aqueous core. The formed microstructures are collected by dissolving the hydrogel template as described for FIG. 1.

As shown in FIG. 3, another method of manufacturing nano- and/or microparticles according to the present invention comprises applying a polymer dissolved in an organic solvent to an inner surface of the plurality of wells of the hydrogel template so that the wells are coated with the polymer. One or more aqueous droplets, which can contain bioactive agent(s) dissolved therein, are provided in the coated wells, e.g., with an ultrasonic atomizer. See, e.g., U.S. Pat. No. 6,767,637, the disclosure of which is incorporated herein by reference. The wells are then filled with the polymer dissolved in organic solvent so that the aqueous droplets become encapsulated by polymer, e.g., by solvent exchange. See, U.S. Pat. No. 6,599,627, the disclosure of which is incorporated herein by reference. Finally, the polymer encapsulated droplets are removed from the hydrogel template, such as by dissolving the template in water, to release the particles.

As shown in FIGS. 1-3, the formed microstructures are collected by simply dissolving the hydrogel template in aqueous solution, and this process makes the large scale production of microstructures simpler and easier than any previous method. The microstructures generated by this method will have negligible amounts of contaminants, if they exist, as it involves the use of a biocompatible hydrogel-forming polymer, such as gelatin, and drug/PLGA in a small quantity of an organic solvent which can be removed by vacuum evaporation. The preparation of microstructures described herein involves the filling of an open mold. An open mold means that the wells in the hydrogel template are open for filling the drug/polymer solution and open for evaporation of the organic solvent used. In the currently available methods, e.g., S-FIL method, the glass template is pressed into a monomer solution forming a closed mold, followed by photopolymerization. This closed mold results in a film formation, requiring several subsequent processing steps, and thus reducing the efficiency of microstructure production. The open molding can reduce the number of steps and sequences of events required during molding of microstructures, and it can improve the evaporation rate of solvent from the precursor material, thereby, increasing the efficiency and rate of microstructure production.

Fabrication of Hydrogel Templates with Tunable Melting Temperatures

Large scale production of microstructures containing hydrophilic macromolecular drugs, such as protein drugs, enzymes, DNA, and siRNA, is very challenging and difficult as these classes of biomolecules are highly sensitive to processing conditions, e.g., high temperature or long-term exposure to organic solvent. The present hydrogel template strategy precisely and perfectly addresses these issues and it can be readily used for the large scale production of microparticles of sensitive biological molecules without denaturing them. By doping hydrogel-forming gelatin solutions with certain inorganic salts, synthetic polymers, or biomolecules, the melting temperatures of the gelatin templates can be modulated to suit specific microparticle production requirements. Furthermore, since the particle harvesting steps are performed in water or aqueous buffer solutions, denaturation of sensitive biomolecules in microparticles can be minimized or avoided, thus retaining their biological activity. Doping hydrogel-forming solutions with other materials can reduce the melting temperature of the gelatin hydrogel templates. Thus, inorganic salts (such as LiCl, NaCl, KCl, $CaCl_2$, and $MgCl_2$), synthetic polymers (such as PVA, PEG, polyethyleneimine, and poly(acrylic acid)), and biomolecules (such as bovine serum albumin, and histidine), can lower the melting temperature of gelatin templates, as shown in the examples below.

Results and Discussion

Successful translation of microfabrication technologies to drug delivery applications requires development of new methods that utilize only mild conditions for processing and use biocompatible materials, and are simple enough for scale-up production. The methods also result in high drug loading efficiency and the ability to control the drug release kinetics. Bioactive agent can be loaded into the microparticles in a range from about 1 to about 80 wt %, preferably about 5 to about 50 wt %. The present invention affords an unexpectedly simple, inexpensive, and efficient hydrogel template strategy for fabrication of polymeric microstructures of the predefined size and shape. The hydrogel forming materials have been used for the first time in preparation of imprinted templates for fabrication of individual microstructures of homogeneous size and shape.

Any material that can form a sol-gel phase-reversible hydrogel can be used in preparing the hydrogel template of the present invention. Exemplary gels include gelatin, agarose and pectin. Some polymers form a hydrogel at higher temperature and melt at lower temperatures. These are called inverse thermoreversible hydrogels and examples include methylcellulose and poly(ethylene oxide)/poly(propylene oxide)/poly(ethylene oxide) triblock copolymers. Other polymers that can form reversible hydrogel in the presence of an organic salt, such as formation of a hydrogel by sodium alginate in the presence of calcium ions, can also be used in the preparation of hydrogel templates. Preferably, gelatin is employed as it possesses properties ideal for fabricating microstructures using the hydrogel template method. Gelatin has a combination of properties, such as reversible gel-to-sol transition of aqueous solution, insolubility in cold water but complete solubility in warm water, and ability to act as a protective colloid. The ability to act as a protective colloid is a very useful property of gelatin that is critically useful in manufacturing of microstructures using the hydrogel template method, as gelatin can adsorb onto the microstructure surface to protect them from aggregation in aqueous solution by steric repulsion.

Hydrogel forming materials have been used in tissue engineering, drug delivery, diagnostics, and as medical and biological sensors. However, hydrogel materials have not been used previously to form micropatterned sacrificial templates. It was generally thought that hydrogels were mechanically too weak to be used as a template for preparing microstructures. Hydrogels usually contain water 10% or higher, and those hydrogels containing more than 95% water are known as superabsorbent. The gelatin hydrogels contain 40-90% water. Because of the presence of a large amount of water, hydrogels are usually assumed to be very weak, and thus, it was thought that hydrogels could not be used as templates for preparing microparticles. Surprisingly, however, gelatin hydrogels provided sufficient mechanical strength for processing.

The major advantages of a hydrogel template strategy are as follows. (1) The sol-gel phase reversible nature, i.e., thermoreversible, or pH reversible, or stimuli responsive attributes, of the hydrogel forming materials enables the simpler template preparation and particle harvesting methods. (2) The hydrogel templates can be made highly elastic and mechanically robust to withstand deformation and fracture, thus allowing their manipulation required for template preparation and filling. (3) The three-dimensional network of the hydrogel templates drastically slows down the diffusion of drug, protein, DNA, siRNA, and polymer precursors from the microwells into the template. (4) The hydrogel template method is applicable to a variety of polymers and in situ polymerizable materials under conditions that do not melt or dissolve the hydrogel. (5) The use of reversible physical gels with desired functional properties, such as pH-sensitivity and temperature sensitivity, for template preparation and particle release enhances the versatility of the strategy.

The following representative examples demonstrate fabricating microstructures using the instant hydrogel template method. Many changes, modifications, and alterations can be employed without departing from the scope of the presently disclosed subject matter.

EXAMPLES

Example 1

Fabrication of Gelatin Hydrogel Template with Wells of Specific Geometry

In a typical fabrication of the hydrogel template, a gelatin solution (30% by weight) was prepared by dissolving 30 g of gelatin (from porcine skin for electrophoresis Type 1, 300 Bloom, Sigma) in a total 100 ml of nanopure water (in a 150 ml Pyrex bottle) and was thoroughly mixed. The bottle was capped to prevent evaporation and placed in an oven at 65° C. for 2 h or until formation of a clear solution. The clear gelatin solution was used to prepare hydrogel templates. This warm and clear gelatin solution (10 ml) was transferred with a pipette onto a microfabricated silicon wafer (3" diameter) containing circular pillars of 50 µm diameter and 50 µm height (FIG. 1A). The gelatin solution was evenly spread to form a thin film completely covering the wafer. This silicon wafer containing gelatin film was cooled to 4° C. for 5 min by keeping it in a refrigerator. Cooling resulted in formation of an elastic and mechanically strong gelatin template. After cooling, the gelatin hydrogel template was peeled away from the silicon wafer (FIG. 1B). The hydrogel template, 3" in diameter, contained circular wells of 50 µm diameter and 50 µm depth. The gelatin hydrogel template was examined under a bright-field reflectance microscope to determine its structural integrity (FIG. 1C). Thus prepared gelatin hydrogel template melted at 45° C.

Example 2

Fabrication of PLGA Microparticles

A 20% PLGA (MW 60,000; IV 0.8, Birmingham Polymers) solution was prepared by dissolving 2 g of PLGA in 10 ml of dichloromethane. Onto a 3" diameter hydrogel template containing circular wells of 50 µm diameter and 50 µm depth, 200 µl of 20% PLGA solution was transferred with a pipette. The PLGA solution was evenly spread on the hydrogel template by swiping with a razor blade at 45° angle. A gentle pressure was applied to force the PLGA solution to completely fill the wells without deforming the hydrogel template (FIG. 1D). Swiping with a razor blade minimizes the PLGA film formation on the hydrogel template surface. The complete filling of the circular wells with PLGA solution and isolated microparticles was observed under a bright-field and fluorescence microscope (Olympus BX51 Microscope).

Example 3

Collection of Microparticles

A hydrogel template filled with 20% PLGA solution was exposed to 25° C. for 10 min to remove dichloromethane from the PLGA microparticles. The gelatin hydrogel template was then placed in a 50 mL beaker containing 25 ml of nanopure water at 45° C. and gently shaken for 2 min to completely dissolve the hydrogel template (FIG. 1E). The temperature for dissolving the gelatin hydrogel templates could be lowered by doping with various agents such as KCl. This step resulted in complete release of individual microparticles. The solution was transferred into a conical centrifuge tube and centrifuged (Eppendorf Centrifuge 5804, Rotor A-4-44, at 5,000 rpm, 19.1 RCF) for 5 min, the supernantant liquid was discarded, and the pellet was collected. The pellet obtained upon centrifugation was freeze dried and stored in a refrigerator. This pellet upon resuspension in 1 ml of nanopure water formed free and isolated microparticle dispersion due to the presence of surface-adsorbed gelatin molecules which function as a colloid stabilizer by steric repulsion (FIG. 1F).

Example 4

Optional Formation of PDMS Elastomeric Molds from Silicon Master Template

As shown in FIG. 2, a poly(dimethyl siloxane) (PDMS) (SYLGARD® 184 silicone elastomer) imprint mold is prepared on top of the Si wafer master template. The blend of elastomeric monomer and curing agent (Sylgard 184 Silicone Elastomer, Dow Corning) in a 10:1 (w/w) ratio is mixed thoroughly. The mixture is poured on top of the Si wafer master template inside a Petri dish (FIG. 2A). The Petri dish is placed in vacuum for 10 min to remove air bubbles, and then transferred to a 70° C. chamber for curing for 30 min. The PDMS imprint mold is peeled off from the Si master template (FIG. 2B), and the PDMS imprint mold is used as a template for preparing a hydrogel template (FIG. 2C) that is used to prepare nano/micro particles as described in Examples 1-3.

Example 5

Fabrication of Nano/Micro Mono-Nuclear Capsules

Nano/micro capsules with an aqueous mono-nucleus core are formed by encapsulating aqueous droplets with biodegradable polymer membranes. Referring to FIG. 3, PLGA is used as a representative polymer. PLGA is dissolved in an organic solvent and the solution is sprayed onto a hydrogel mold using a spin coater or an ultrasonic atomizer (FIG. 3B). The PLGA solution forms a thin film on the hydrogel mold. Because of the interfacial tension between water and an organic solvent, most organic solvent spreads on the surface of the hydrogel. Since there are many solvents that can be used in this process, a number of solvents were screened to find the best solvent for formation of the PLGA film. A PLGA copolymer (75/25) was synthesized and dissolved in various organic solvents to prepare a 2% solution. The hydrogel mold is made of gelatin at a 30% concentration.

Once the first PLGA film is formed on a hydrogel mold, aqueous droplets containing bioactive agents, including pharmaceutically active agents or imaging agents, are sprayed onto the first PLGA film (FIG. 3C). Because of high surface tension of aqueous droplets, they remain as spherical droplets after filling each hole. Once the holes are filled with aqueous solution, another PLGA film is formed by the same process (FIG. 3D). This results in formation of an aqueous droplet surrounded by a PLGA layer in each well, i.e., a microcapsule with an aqueous core surrounded by a PLGA film.

After the second PLGA film is formed on the aqueous droplets, it is possible that the PLGA film covers all over the hydrogel mold, including the space between the wells. In this case, to separate individual microcapsules, the film between the capsules is removed by exposing the whole hydrogel mold to oxygen plasma etching. Oxygen plasma etching for a few minutes degrades a thin layer of PLGA while leaving the capsules intact. The hydrogel mold with PLGA capsules in wells is then placed in a water bath to dissolve the gelatin mold. When the gelatin mold is dissolved, gelatin molecules can adsorb to the surface of individual capsules providing steric repulsion against aggregation of the formed capsules. Other techniques currently available do not provide any means of stabilizing the capsules using the hydrogel mold.

Example 6

Fabrication of Gelatin Hydrogel Templates with Tunable Melting Temperatures

In a typical fabrication of a gelatin template doped with an agent that can alter the melting temperature of the gelatin gel, different inorganic salt and biological agents were dissolved in 100 ml of Nanopure water contained in a 150 ml Pyrex bottle. The different agents are listed in Table 1. To this solution 30 g of gelatin (from porcine skin for electrophoresis Type 1, 300 Bloom, Sigma) was added and thoroughly mixed. The bottle was capped to prevent evaporation and placed in an oven at 55° C. for 2 h or until the formation a clear solution. The clear gelatin solution was used to prepare hydrogel templates. This warm and clear gelatin solution (10 ml) was transferred with a pipette onto a microfabricated silicon wafer (3" diameter) containing circular pillars of 50 μm diameter and 50 μm height. The gelatin solution was evenly spread to form a thin film completely covering the wafer. This silicon wafer containing gelatin film was cooled to 4° C. for 5 min by keeping it in a refrigerator. Cooling resulted in formation of an elastic and mechanically strong gelatin template. After cooling, the gelatin hydrogel template was peeled away from the silicon wafer. The hydrogel template, 3" in diameter, contained circular wells of 50 μm diameter and 50 μm depth. The gelatin hydrogel template was examined under a brightfield reflectance microscope to determine its structural integrity. The gelatin hydrogel templates prepared in the presence of different agents melted at temperatures lower than 45° C. as shown in Table 1.

TABLE 1

The melting temperature of gelatin hydrogel plates (30% gelatin) using different doping agents.

| Doping agent | Melting temperature |
| --- | --- |
| None (control) | 45° C. |
| 5 g of KCl (99+% purity, Aldrich) | 29-31° C. |
| 5 g of NaCl (99% purity, Mallinkrodt) | 35-36° C. |
| 5 g of LiCl (99% purity, Aldrich) | 35-37° C. |
| 2 g of Bovine serum albumin (98% purity, Sigma) | 32-34° C. |

Example 7

Fabrication of PLGA Microparticles in Various Shapes

Figure 4:
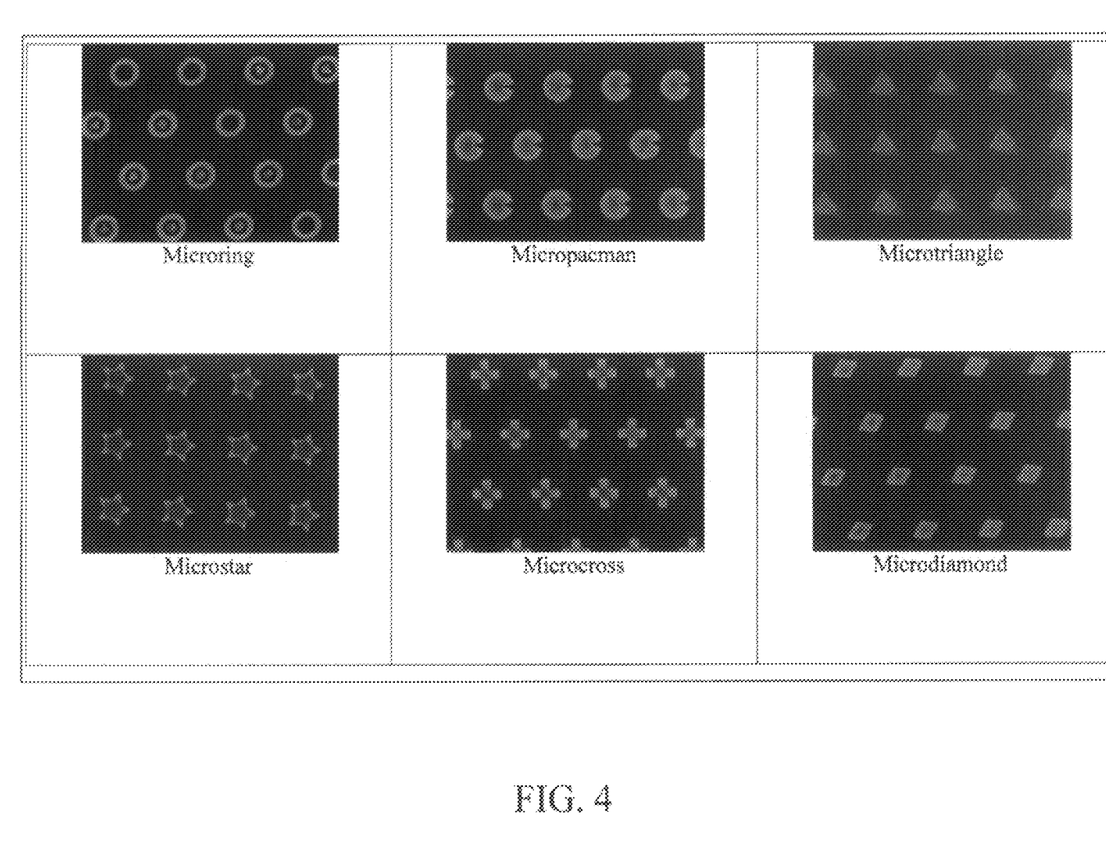
FIG. 4 shows fluorescence images of gelatin hydrogel templates provided with microwells of various geometries. The wells are filled with PLGA solution doped with nile red, a fluorescent dye, for easy visualization. All the wells are 50 µm in diameter and 50 µm in depth.

Microparticles of various shapes were prepared, and exemplary shapes are shown in FIG. 4. As shown, microparticles in the shape of ring, pacman, triangle, star, cross, and diamond could be easily prepared. In addition to these shapes, microparticles with others such as common circle and square could also be easily prepared.

Example 8

Fabrication of Polycaprolactone (PCL) Microparticles

A 20% PCL (d 1.145, Aldrich) solution was prepared by dissolving 2 g of PCL in 10 ml of dichloromethane. The same process was used to make microparticles as described in Examples 1-3.

Example 9

Fabrication of PLGA Microparticles of Different Sizes

The microparticle size was varied from 1.2 μm to more than 50 μm by simply varying the size of microstructures of the silicon master template. Changing the size from 1.2 μm and higher could be easily done by using UV photolithography, but for sizes smaller than 1.2 μm were made using e-beam lithography.

Example 10

Fabrication of Drug-Loaded PLGA Microstructures

A 20% PLGA (MW 60,000; IV 0.8, Birmingham Polymers) solution was prepared by dissolving 2 g of PLGA in 10 ml of dichloromethane. To this solution was added 1 ml felodipine (1 g/ml in $CH_2Cl_2$) and thoroughly mixed by vortexing to obtain felodipine/PLGA solution (1:2 w/w). Onto a 3" diameter hydrogel template containing circular wells of 50 μm diameter and 50 μm depth was transferred 200 μl of felodipine/PLGA solution with a pipette. The felodipine/PLGA solution was evenly spread on the hydrogel template by swiping with a razor blade. A gentle pressure was applied to force the PLGA solution to completely fill the wells without deforming the hydrogel template. In addition to felodipine, other drugs, such as progesterone, griseofulvin, probucol and paclitaxel, were also incorporated into microstructures.

Example 11

Figure 5:
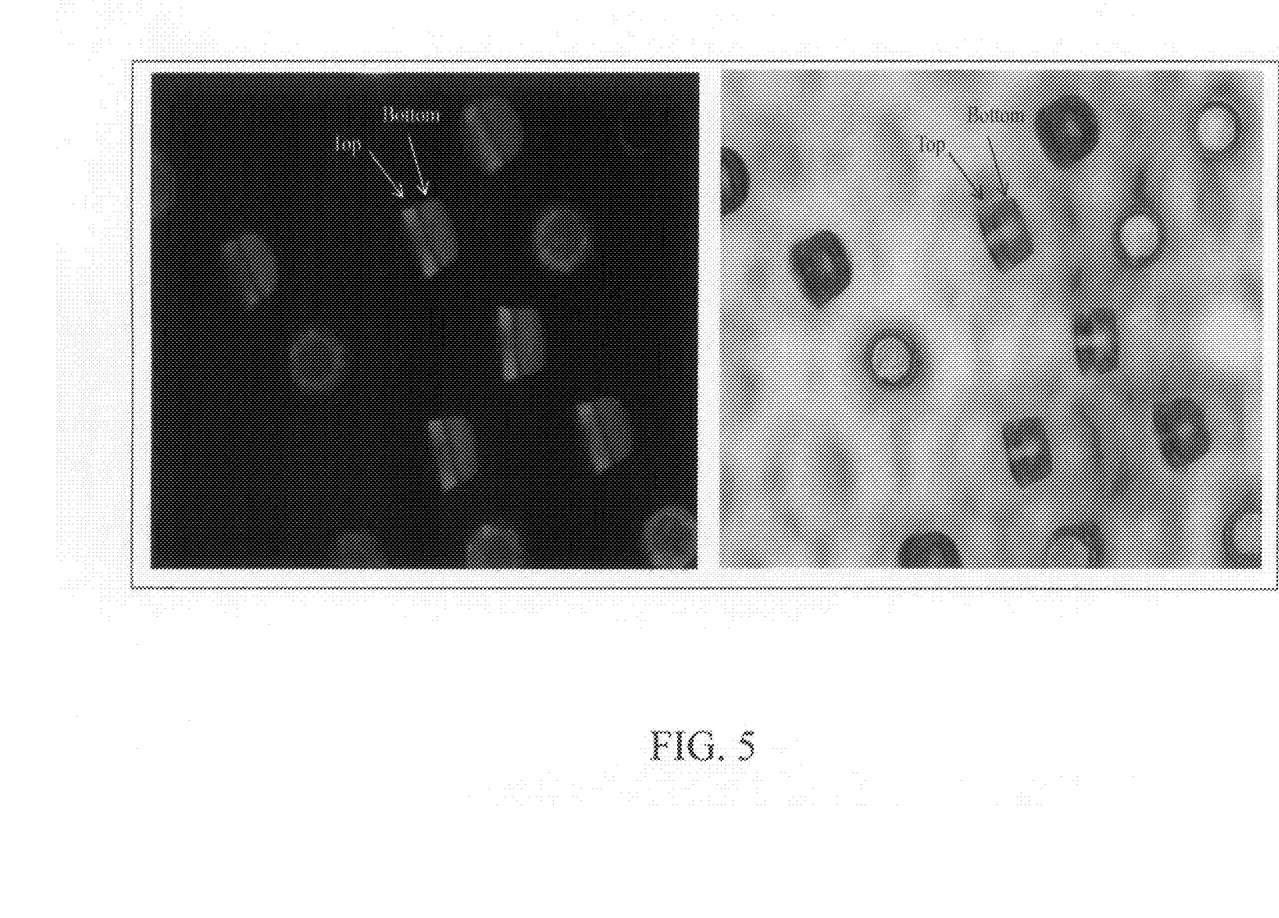
FIG. 5 shows fluorescence (left) and bright-field (right) images of bilayer PLGA microdiscs formed according to principles of the present invention. The microdiscs contain two distinct layers of Nile red dye (red, top) and felodipine drug (blue, bottom).

Fabrication of Microstructures with a Bilayer of Two Different Drugs or Dyes A gelatin hydrogel template was also used to fabricate bilayer microstructures having two distinct layers of two different drugs, or a drug and a dye, or two different dyes. The same method described in Examples 1-3 was used to prepare bilayer PLGA microdiscs of felodipine drug and nile red dye. Preparation of bilayer microparticles is unique to the hydrogel template approach because it is very difficult to prepare using currently available methods. The fluorescence and bright-field images in FIG. 5 clearly demonstrate the presence two clear and distinct layers of felodipine (blue) and Nile red (red).

Example 12

Large-Scale Manufacturing of Hydrogel Templates and Microstructures

A gelatin solution (30% by weight) was prepared by dissolving 30 g of gelatin (from porcine skin for electrophoresis Type 1, 300 Bloom, Sigma) in 100 ml of nanopure water (in a 150 ml Pyrex bottle) and was thoroughly mixed. The bottle was capped to prevent evaporation and placed in an oven at 65° C. for 2 h or until the formation a clear solution. The clear gelatin solution thus prepared was filled into a thin layer chromatography plate coater (Camag). Using the gelatin-filled plate coater a hydrophilic plastic sheet (20 cm×20 cm; 3M Corporation) was coated with a 300 μm thick gelatin layer. Microfabricated silicon wafers (3" diameter) containing circular pillars of 50 μm diameter and 50 μm height were pressed into the gelatin film and cooled to 4° C. for 5 min by keeping it in a refrigerator. Cooling resulted in the formation of elastic and mechanically strong gelatin template. After cooling, the gelatin hydrogel template was peeled away from the silicon wafers. The hydrogel template thus obtained was 20 cm×20 cm in size, and contained circular wells of 50 μm diameter and 50 μm depth. Thus prepared hydrogel template was filled with a polymer solution followed by the melting of the hydrogel template to collect the formed microparticles.

Novelty and Advantages

This novel approach uses a hydrogel template for fabricating microparticles. The hydrogel template not only serves as a template for making microparticles, but also serves as a stabilizing component for microparticles suspended in the aqueous solution at the end of the process. Another critical process in this approach is to solidify a biodegradable polymer while it is in the microcavities of the hydrogel template. This approach has minimal contact with water until the last step when the whole hydrogel template is dissolved to release individual microparticles. This particular process is responsible for high loading efficiency of drugs into the particles. Not only biodegradable polymers, but also inert polymers, such as poly(ethylene-co-vinyl acetate), nylon, silicone rubber, and polystyrene can be used to form particles depending on the intended applications.

The microfabrication process utilizes a silicon wafer master template, and the shape and size of the cavities formed in the silicon template can be easily controlled, and the size distribution will be very homogeneous. The size can be varied from nanometers to micrometers, and the shape can be varied from simple disc to more complex shapes, such as star or cross. The ability to control the size and shape on the master template, i.e., the hydrogel mold, along with the ability to load various active ingredients makes this novel microfabrication method highly useful.

The present invention has been described with reference to specific examples for purposes of clarity and understanding. It should be appreciated by the skilled practitioner that certain modifications and improvements can be practiced within the scope of the appended claims and equivalents thereof.

REFERENCES

The pertinent portions of the following references are incorporated herein by reference.

H. Schift, Nanoimprint lithography: An old story in modern times? A review. J. Vac. Sci. Technol. B26 (2008) 458-479.

V. N. Truskett, P. C. Watts, Trends in imprint lithography for biological applications. Trends Biotechnol. 24 (2006) 312-317.

C. D. Schaper, Molecular transfer lithography for pseudo-maskless, high-throughput, aligned nanolithography. J. Vac. Sci. Technol. B21 (2003) 2961-2965.

Y. Xia, G. M. Whitesides, Soft lithography. Annu. Rev. Mater. Sci. 28 (1998) 153-184.

L. Yan, W. T. S. Huck, X.-M. Zhao, G. M. Whitesides, Patterning thin films of poly(ethylene imine) on a reactive SAM using microcontact printing. Langmuir 15 (1999) 1208-1214.

X.-M. Zhao, Y. Xia, G. M. Whitesides, Fabrication of three-dimensional micro-structures: Microtransfer molding. Adv. Mater. 8(10) (1996) 837-840.

M. Wang, H.-G. Braun, T. Kratzmüller, E. Meyer, Patterning polymers by micro-fluid-contact printing. Adv. Mater. 13 (2001) 1312-1317.

J. Guan, A. Chakrapani, D. J. Hansford, Polymer microparticles fabricated by soft lithography. Chem. Mater. 17 (2005) 6227-6229.

J. P. Rolland, et al., Direct fabrication and harvesting of monodisperse, shape-specific nanobiomaterials. J. Am. Chem. Soc. 127 (2005) 10096-10100.

J. Y. Kelly, J. M. DeSimone, Shape-specific, monodisperse nano-molding of protein particles. J. Am. Chem. Soc. 130 (2008) 5438-5439.

What is claimed is:

1. A method of making drug-containing microparticles comprising:
   (a) filling a plurality of wells provided in a preformed, dissolvable hydrogel mold with a non-aqueous solution or a paste containing polycaprolactone, at least one drug and a nonaqueous solvent, which hydrogel mold is formed of a sol-gel phase reversible hydrogel comprising gelatin;

(b) solidifying the composition in the plurality of wells by evaporating the nonaqueous solvent, thereby forming microparticles; and (c) harvesting the microparticles from the preformed hydrogel mold by dissolving the hydrogel mold in an aqueous solution.

2. The method of claim 1, wherein the drug is selected from felodipine, paclitaxel, sirolimus, probucol, progesterone, and griseofulvin.

3. The method of claim 1, wherein the drug is present in the microparticles in the range of about 1 to about 80 wt %.

4. The method of claim 3, wherein the drug is present in the microparticles in the range of about 5 to about 50 wt %.

5. The method of claim 1, wherein the microparticles have a diameter in the range of about 0.5 μm to about 100 μm.

6. The method of claim 5, wherein the microparticles have a diameter in the range of about 1 μm to about 50 μm.

7. The method of claim 1, wherein the harvested microparticles have gelatin molecules adsorbed to their surface.

8. The method of claim 1, wherein said harvesting comprises filtering and/or centrifugation of the microparticles from the aqueous solution.

9. The method of claim 1, wherein the nonaqueous solvent is dichloromethane.

10. The method of claim 1, wherein the hydrogel mold is prepared by:
  (a) forming a master template provided with a plurality of microstructures;
  (b) coating the master template with a layer of an aqueous gelatin solution;
  (c) converting the aqueous gelatin solution to gel by lowering the temperature to form the hydrogel mold; and
  (d) separating the hydrogel mold from the master template, which hydrogel mold is provided with a plurality of wells.

11. The method of claim 1, wherein the hydrogel mold is prepared by:
  (a) forming a master template provided with a plurality of microstructures;
  (b) forming a polymer template as a negative image of the master template and separating the polymer template from the master template, which polymer template comprises poly(dimethyl siloxane);
  (c) coating the polymer template with a layer of an aqueous gelatin solution;
  (d) converting the aqueous gelatin solution to gel by lowering the temperature to form the hydrogel mold; and
  (e) separating the hydrogel mold from the polymer template, which hydrogel mold is provided with a plurality of wells.

12. The method of claim 1, wherein the harvested microparticles are of homogeneous size.

13. The method of claim 1, wherein the harvested microparticles are of homogeneous shape.

14. A method of making drug-containing microparticles comprising:
  (a) filling a plurality of wells provided in a pre-formed, dissolvable hydrogel mold with a nonaqueous solution or a paste containing polycaprolactone, and at least one drug dissolved in a nonaqueous solvent, which hydrogel mold is formed of a sol-gel phase reversible hydrogel comprising gelatin;
  (b) solidifying the nonaqueous solution containing polycaprolactone and the at least one low molecular weight drug in the wells by evaporating the nonaqueous solvent; and
  (c) harvesting the microparticles from the pre-formed hydrogel mold by dissolving the hydrogel mold in aqueous solution,
  wherein the harvested microparticles have a diameter in the range of about 0.5 μm to about 100 μm.

15. The method of claim 1 wherein the composition is a solution.

16. The method of claim 14, wherein the harvested microparticles are of homogeneous size.

17. The method of claim 14, wherein the harvested microparticles are of homogeneous shape.

* * * * *